US00PP37672P2

(12) United States Plant Patent
Byrne et al.

(10) Patent No.: US PP37,672 P2
(45) Date of Patent: Sep. 8, 2026

(54) PEACH TREE NAMED 'TRH3C111'

(50) Latin Name: *Prunus persica.*
Varietal Denomination: TRH3C111

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,377

(22) Filed: Sep. 22, 2025

(51) Int. Cl.
*A01H 5/08* (2018.01)

(52) U.S. Cl.
USPC ..... Plt./197

(58) Field of Classification Search
USPC ..... Plt./156, 180, 194, 197
See application file for complete search history.

(56) References Cited

U.S. PATENT DOCUMENTS

PP28,077 P3 6/2017 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Rouse and Sherman. 1989. 'TropicBeauty': A low-chilling peach for subtropical climates. HortSci. 24(1): 165-166.

*Primary Examiner* — Karen M Redden
(74) *Attorney, Agent, or Firm* — Dentons US LLP

(57) ABSTRACT

Disclosed is a new variety of *Prunus persica* named 'TRH3C111'. This new variety, which requires approximately 300 chilling units of dormancy, is considered to be a peach tree of early mid-season maturity, which produces yellow fleshed, subacid fruit that are firm, with 70-90% dark orange red blush over an orange-yellow ground color, and suitable for the fresh fruit market.

5 Drawing Sheets

Latin name of the genus and species of the plant claimed: *Prunus persica.*

Variety denomination: 'TRH3C111'.

CROSS-REFERENCE TO RELATED APPLICATIONS

Peach trees developed under the same breeding program as 'TRH3C111' include the co- pending applications listed below.

| U.S. application Ser. No. | Title |
|---|---|
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,368 | PEACH TREE NAMED 'TRH3E88LW' |
| U.S. 19/336,370 | PEACH TREE NAMED 'TX2B449LW' |
| U.S. 19/336,385 | PEACH TREE NAMED 'TRH2B102LW' |
| U.S. 19/336,372 | PEACH TREE NAMED 'TX2C465CW' |
| U.S. 19/336,375 | PEACH TREE NAMED 'TRH1C104LW' |

-continued

| U.S. application Ser. No. | Title |
|---|---|
| U.S. 19/336,380 | PEACH TREE NAMED 'TRH2C108W' |
| U.S. 19/336,383 | PEACH TREE NAMED 'TRH2E116L' |

BACKGROUND OF THE INVENTION

This invention relates to peach trees and, more specifically, to peach trees referred to as a variety of *Prunus persica* named 'TRH3C111', which requires approximately 300 chilling units of dormancy, produces firm, semi-freestone, subacid, yellow-flesh peach with 70-90% dark orange red blush over an orange-yellow ground color that matures early mid-season. The present peach tree was the result of an ongoing Stone Fruit Breeding Program at College Station, Brazos County, Texas. To this end, controlled crosses were made each year to produce seedling populations from which improved progenies are evaluated and selected. The seedling 'TRH3C111' was derived from a cross between a low-chill, yellow-flesh, acid, peach selection 'TX2B136' (not patented) and a low chill, subacid, white-fleshed nectarine, 'Smooth Delight One' (patented, U.S. Plant Pat. No. 28,077). 'TX2B136' was a seedling selected from a cross between the low chill cultivar 'Hermosillo' (not patented, Sherman, W. B., J. Rodriguez-Alcazar, and B. L. Topp. 1992. Peaches and nectarines developed but not introduced by the University of Florida. Fruit Varieties Journal 46:124-127) and the low chill peach selection 'TXW1293-1' (not patented). 'TXW1293-1' was a low-chill, selection made from a large open pollinated population of seedlings with 'Tropic Beauty' (not patented, Rouse, R. E. and W. B. Sherman. 1989. 'TropicBeauty': A low-chilling peach for subtropical climates. HortSci. 24(1): 165-166,) as a female parent. The seed from the cross between 'TX2B136' and 'Smooth Delight One' were embryo cultured and planted in 2011 in an experimental plot in Floresville, TX. 'TRH3C111' was marked for subsequent observation and noted as having exceptional characteristics in 2013.

'TRH3C111' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2019), Somerville (2016-2020) and Fairfield (2015-2020), Texas. This evaluation clearly demonstrated that the re-propagated trees were true to the characteristics of the original seedling in all observable aspects.

SUMMARY OF THE INVENTION

The 'TRH3C111' peach produces subacid, yellow-fleshed fruit that ripens in the early mid-season; is considered firm and has a 70-90% dark orange red blush over an orange-yellow ground color. In this regard, the present variety of peach tree bears fruit that are ripe for commercial harvesting and shipment in late May to early June, when the fruit is grown in the medium chill zone of Texas. 'TRH3C111' blooms ~5 days after its pollen parent 'Smooth Delight One' (patented, U.S. Plant Pat. No. 28,077) and ~6 days before its female parent 'TX2B136' (not patented). It ripens 3-4 weeks after its parents. 'TRH3C111' differs from its yellow-fleshed, acid, peach female parent as it has subacid flesh and differs from its female white-fleshed, subacid nectarine pollen parent as it is a yellow-fleshed peach. 'TRH3C111' as compared to the medium chill peach cultivar 'Texking' (patented, U.S. Plant Pat. No. 14,627), it has a low acid versus a traditional acid flavor, has reniform versus globose glands, blooms ~2 weeks before and ripens 2½ weeks later than 'Texking'. 'TRH3C111' compared to 'White Delight Two' (not patented, US 2016/0205832 P1, abandoned) as it has yellow versus white flesh, reniform versus globose glands, showy versus non showy flowers, requires 250 less chilling hours and blooms 3 weeks earlier than 'White Delight Two'. 'TRH3C111' as compared to 'TRH2E121L' (U.S. Ser. No. 19/336,358) a selection with the same parentage, blooms about a week earlier and requires 150 fewer chill hours to fruit than 'TRH2E121L'. 'TRH3C111' is also related to two other co-pending cultivars 'TRH1C104LW' (U.S. Ser. No. 19/336,375) and 'TRH2E116L' (U.S. Ser. No. 19/336,383) as they have the reciprocal parentage of 'Smooth Delight One' x 'TX2B136'. 'TRH3C111' differs from 'TRH1C104LW' as it has yellow versus white flesh and ripens 5 days earlier than 'TRH1C104LW'. 'TRH3C111' differs from 'TRH2E116L' as it has more petiolar leaf glands, blooms earlier and requires 100 less chilling units for proper fruiting than 'TRH2E116L'. This new subacid, yellow-fleshed peach exhibits potential to be commercialized in regions that have chilling accumulations that are relatively low.

BRIEF DESCRIPTION OF THE DRAWINGS

This new variety of peach tree is illustrated by the accompanying photographs of 3-year old to 5-year old plants grown in Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
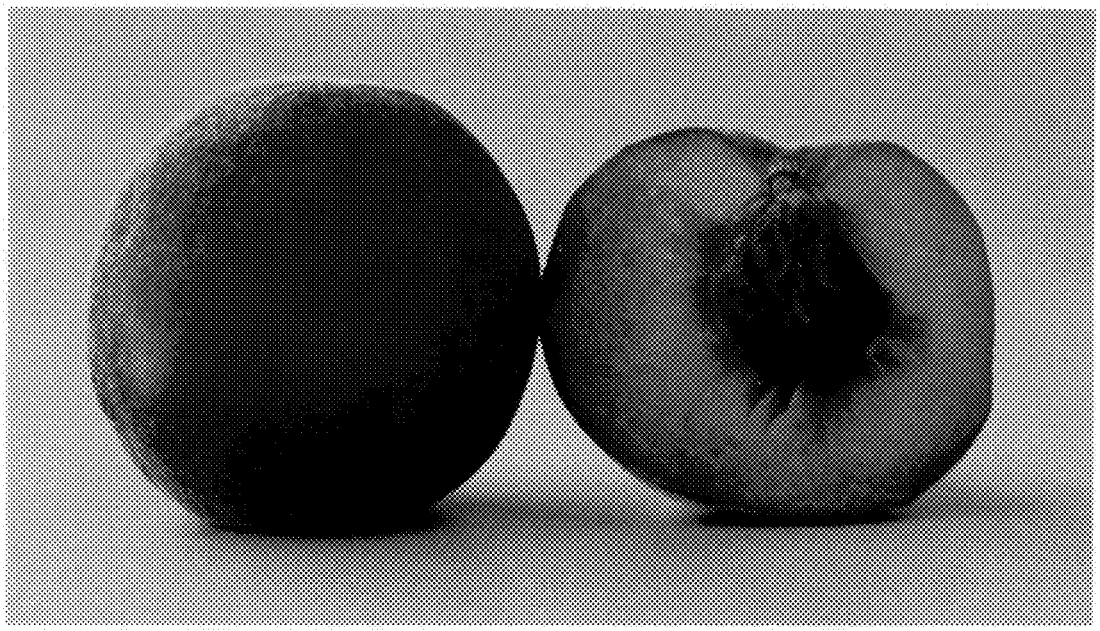
FIG. 1 Fruit of 'TRH3C111' produced in Pleasanton, Texas showing external and internal coloration.
Figure 2:
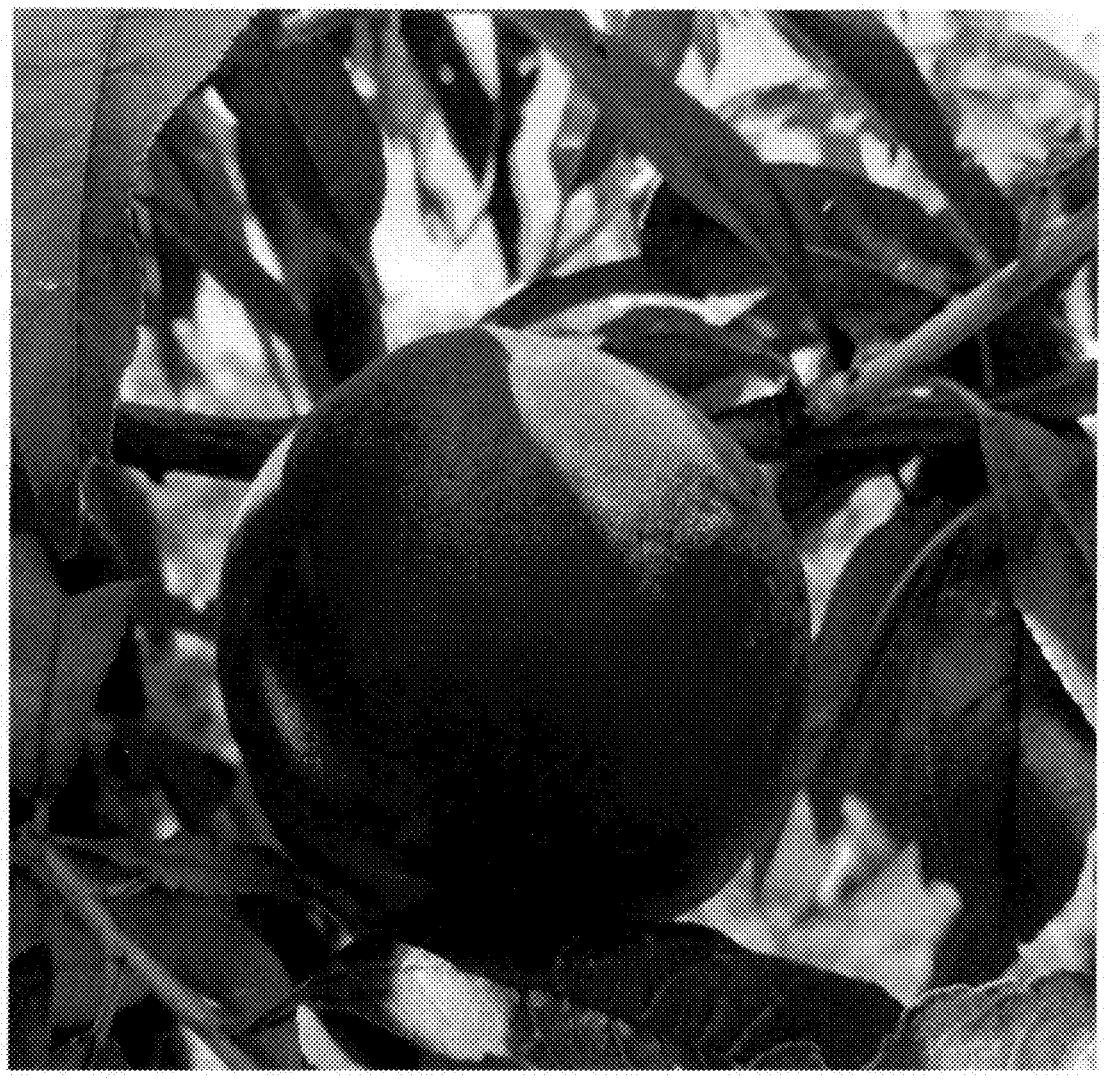
FIG. 2 'TRH3C111' fruit produced in Pleasanton, Texas.
Figure 3:
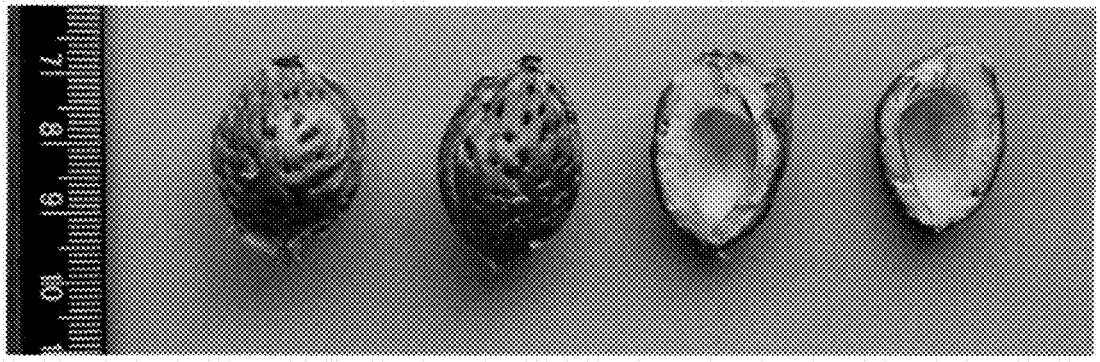
FIG. 3 Photograph of the endocarps of the 'TRH3C111' peach. The ruler is in centimeters.
Figure 4:
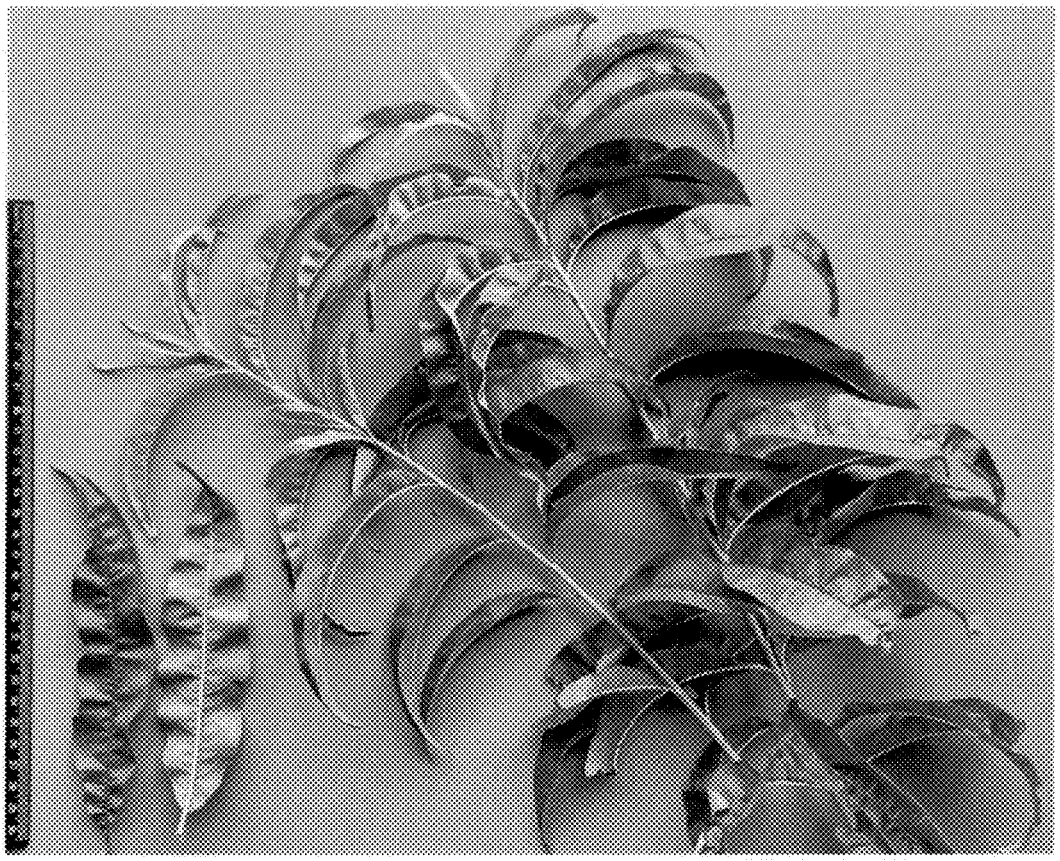
FIG. 4 A stem showing the leaves of the 'TRH3C111' peach. The ruler is in centimeters.
Figure 5:
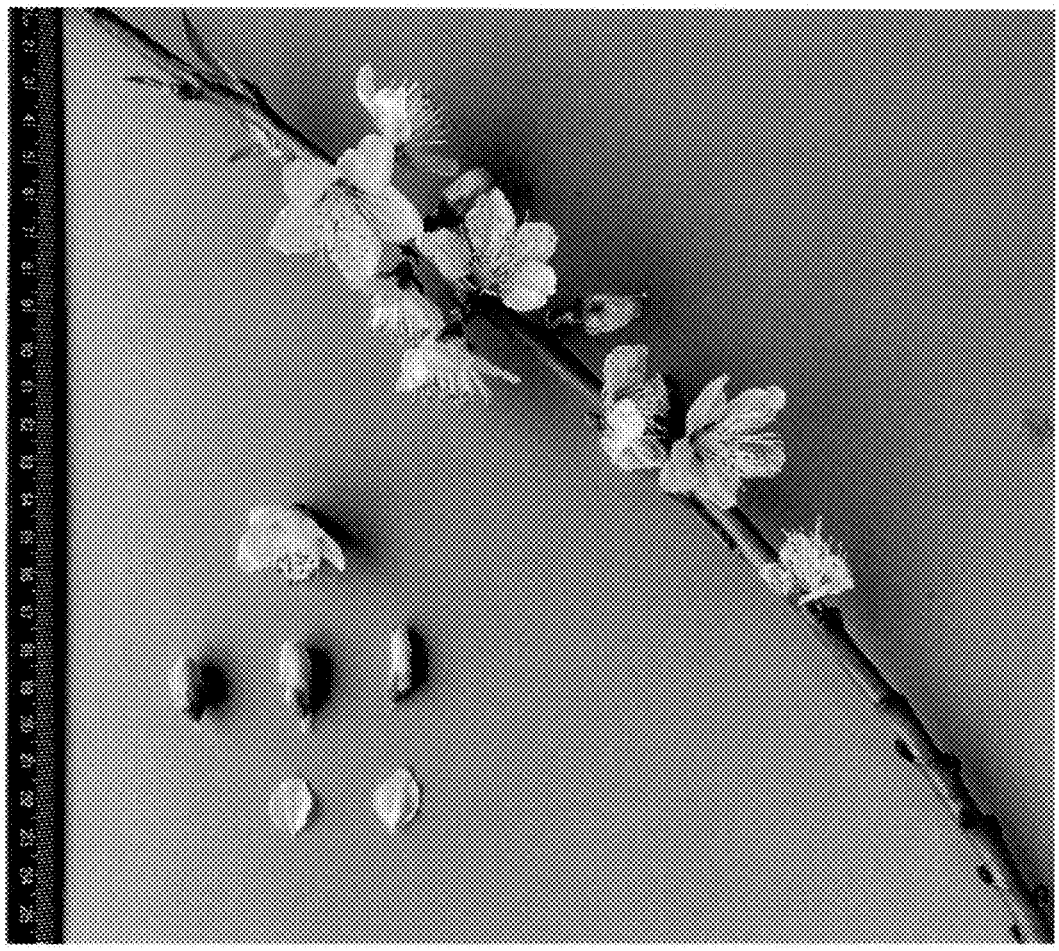
FIG. 5 A stem showing the flowers of the 'TRH3C111' peach. The ruler is in centimeters.

Referring more specifically to the pomological details of this new and distinct variety of peach tree, the following has been observed under the ecological conditions prevailing at the experimental orchards in the medium chill zone of Texas. All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars grown in the medium chill zone of Texas.

*Height*.—9 to 10 feet (2.7 to 3.0 m) at the end of the 2024 growing season.

*Width*.—6 feet width (1.8 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH3C111' peach has been trained an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 2 to 3.5 feet (0.6-1.1 m). Average vigor as compared to other commercial peach cultivars grown in the medium chill zone of Texas.

*Regularity of bearing*.—Regular in the absence of temperatures of 28° F. or below during bloom and considered hardy in the medium chill zone of Texas.

Trunk:

*Size*.—Approximately 3 inches (7.6 cm) in diameter and 12.5 inches (31.8 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration* (*RHS*2001).—Variable, colors present are 156A, 156B, 156C, 156D of the Greyed-White Group, 157A, 157B, 157C of the Green-White Group and 183B, 183C, 183D and 187A of the Greyed-Purple Group.

Branches:

*Thickness*.—Average (about 5.1 cm in diameter as measured 10 cm from the trunk on a three-year old tree) as compared to other varieties.

*Surface texture*.—Average and appearing furrowed on wood that is several years old.

*Lenticels*.—Numerous flat, oval lenticels present. The lenticels range in size from approximately 9 to 12 mm in width and were approximately 2 to 3 mm in height.

*Current season shoots*.—Surface texture — Substantially glabrous.

*Internode length*.—Approximately 1.0 to 2.0 cm as measured in the middle of a current season stem.

*Color of mature branches*.—The predominant colors (RHS2001) are 156A, 156B, 156C, 156D of the Greyed-White Group, 166A and 176A of the Greyed-Orange Group, 178A of the Greyed-Red Group and 183A, 183B, 183C of the Greyed-Purple Group.

*Current season shoots*.—Color — Light to medium green (144A, 144B, N144C and N144D of Yellow-Green Group) with some reddish-brown coloration appearing on exposed surface of the shoots (166A of the Greyed-Orange Group).

Leaves:

*Size*.—Considered moderately large for the species. Leaf measurements have been taken from vigorous upright current season growth approximately at mid-shoot.

*Leaf length*.—Approximately 166 to 199 mm.

*Leaf width*.—Approximately 37 to 43 mm.

*Leaf thickness*.—Less than 1 mm.

*Leaf form*.—Lanceolate.

*Leaf tip form*.—Acuminate.

*Leaf upper surface color* (*RHS*2001).—Green varying among 137A, 137B, 137C of the Green Group and 146A of the Yellow-Green Group.

*Leaf lower surface color* (*RHS*2001).—Green varying among 146A, 147B and 147C of the Yellow-Green Group.

*Leaf lower mid-vein color*.—Light yellow green (154C, 156D of the Yellow-Green Group).

*Leaf margins*.—Form — Considered crenate. Uniformity — Considered generally uniform.

*Leaf petioles*.—Length — Approximately 12 to 16 mm. Thickness — Approximately 2 mm. Texture — Glabrous. Color (RHS2001) — Pale green (154C, 156D Group Yellow-Green Group).

*Leaf glands*.—Size — Approximately 1 to 2 mm in height and 0.5 to 1 mm in width. Number — Generally 3 to 5 per leaf. Type — Reniform. Color (RHS2001) — Brown, 166A of the Greyed-Orange Group, N199B of the Grey-Brown Group and 200B, 200C of the Brown Group.

*Leaf stipules*.—Length — Approximately 8 to 12 mm. Form — Lanceolate. Color (RHS2001) — Abaxial/adaxial. Light green (N144C, N144D, 145A and 146D of the Yellow-Green Group) with reddish brown tips (179A and 180A of the Greyed-Red Group and 183A. 183B, 183C, 184A. 184B, 185A and 185B of the Greyed-Purple Group). The stipules are early deciduous. Ratio of flower buds to vegetative buds — Generally 2 flower buds per vegetative bud.

Flowers:

*Floral buds*.—General — The floral buds are conic in form, and slightly appressed relative to the bearing shoot. Color (RHS2001) — The mature buds are tan to medium brown, (approximately 165A, 165B, 166B, 166C and N167A of the Grey-Orange Group, 199A, 199B and N199C of the Grey-Brown Group and 200D of the Brown Group). Mature Bud Length — Approximately 4 to 6 mm. Mature Bud Width — Approximately 1 to 2 mm.

*Blooming type*.—Mean date of full bloom in the medium chill zone of Texas was in early to mid-February (February 9$^{th}$ at Somerville experimental plot), 8 to 13 days before the commercial cultivars 'Texking' (patented, U.S. Plant Pat. No. 14,627) and 'Flordaking' (not patented, Andrews, C. P. 1979. 'Flordaking' peach. HortScience 14(1):81-82).

*Flower type*.—Showy.

*Flower size*.—Flower diameter at full bloom is approximately 30 to 37 mm.

*Bloom quantity*.—Considered abundant.

*Flower bud frequency*.—Normally 2 per node.

*Petal size*.—Width — Approximately 11 to 12 mm. Length — Approximately 16 to 18 mm.

*Petal form*.—Broadly ovate.

*Petal count*.—Nearly always 5.

*Petal abaxial/adaxial color* (*RHS*2001).—Medium pink when young (62C, 62D, 65A, 69A and 73D of the Red-Purple Group), becoming darker with advanced senescence.

*Petal claw*.—Form — The claw is considered truncate in shape. Length — Approximately 1 to 2 mm. Width — Approximately 1 to 2 mm.

*Petal margins*.—Generally considered variable, from nearly smooth to slightly undulate.

*Petal apex*.—Generally — The petal apices appear rounded.

*Flower pedicel*.—Length — Average length of approximately 2 mm. Thickness — Approximately 1 to mm. Color (RHS2001) — Light green (N144B, B144C, N144D, 145A and 145B of the Yellow-Green Group).

*Floral nectaries*.—Color (RHS2001) — Medium to dark orange (25A, 25B, N25A, N25B, N25C, 28A and 28B of the Orange Group and N30D of the Orange-Red Group). Sepal number — Generally five per flower.

*Sepals*.—Surface Texture — The surface has a short, fine, wooly texture. Size — Average Height 4.5 mm, Width 3.8 mm Form — Ovate. Color (RHS2001) — Maroon and green with white (approximately 59A, 59B, 60A, 60B and 71A of the Red-Purple Group; 144B, 144C and N144A of the Yellow- Green Group; 155A, 155B, 155C, 155D of the White Group; 183A, 183B, 184A, 185A, 185B, 187B and 187C of the Greyed-Purple Group).

*Floral cup* (*hypanthium*).—Surface Texture — Generally glabrous. Color (RHS2001) — Maroon with green (approximately 59A, 59B, 60A, 60B and 71A of the Red-Purple Group; 144B, 144C and N144A of the Yellow-Green Group; 183A, 183B, 184A, 185A, 185B, 187B and 187C of the Greyed-Purple Group).

*Anthers*.—Color (RHS2001) — Dark red (approximately 58A, 59C, 60A, 60B and 63A of the Red-Purple Group; 34A and N34A of the Orange-Red Group and 45A, 46A and 46B of the Red Group).

*Pollen production*.—Pollen is abundant, and dried, is a medium-yellow color (RHS2001) (approximately 4A, 4B, 5B, 5C, 6B and 6C of the Yellow Group).

*Filaments*.—Size — Variable in length, approximately 12 to 18 mm, with the filaments about equal to the pistil length and below the petal height. Color (RHS2001) — White (approximately 155A, 155B, 155C, 155D of the White Group) and darkening with advanced maturity.

*Pistil*.—General — About equal to the general anther height and below the height of the petals. Length — Approximately 14 to 18 mm, including the ovary. Color (RHS2001) — Considered a light green-yellow when young (approximately 1A, 1B, 1C, 1D of the Green-Yellow Group), and becoming slightly darker with advancing senescence.

*Surface texture*.—The variety has a long, silver white pubescent pistil (RHS2001) (approximately 155A, 155B, 155C, 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in late May to early June. The average ripe date at Pleasanton, Somerville, and Fairfield were May 27$^{th}$, June 3$^{rd}$ and June 4$^{th}$, respectively.

*Size*.—General — Medium large to large for the season and considered uniform. Average Cheek Diameter — Approximately 54 to 58 mm. Average Suture Diameter — Approximately 55 to 56 mm. Average Axial Diameter — Approximately 46 to 54 mm.

*Fruit form*.—Generally considered oblate. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex and appears deeper at the apex, forming a shallow basin at the apical point. No apparent callusing or stitching exists along the suture line. Fruit suture depth — at midpoint it has a depth of less than 1 mm. Color (RHS2001) — The suture normally is the same color as the underlying blush. Best represented by the following colors: N34A of the Orange-Red Group, 46A and 53A, 53B of the Red Group, 60A of the Red-Purple Group and 183A, 183B, 185A and 187B.

*Ventral surface*.—Form-Considered uniform.

*Stem cavity*.—Width — Approximately 12 to 13 mm. Length — Approximately 18 to 19 mm. Depth — Approximately 6 to 9 mm.

*Fruit base*.—Generally considered flat.

*Fruit apex*.—Generally considered flat.

*Fruit stem*.—Length — 7 to 9 mm. Thickness — Approximately 3 mm. Color (RHS2001) — Light green, approximately 144A, 144B, 145A and 145B of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Not observed. Skin Color — Generally-Variable, with approximately 70-90% of the fruit surface covered with a dark orange-red blush. Blush Color (RHS2001) — This marbled to solid over color is dark orange-red color has many degrees of shading and blending occurring between the following colors: N34A of the Orange-Red Group, 46A, 46B and 53A of the Red Group, 59A, 59B of the Red-Purple Group and 183A, 183B of the Greyed-Purple Group. Skin Ground Color (RHS2001) — The skin ground color is a medium orange-yellow (Yellow Groups 5D, 6D, 7D, 8C, 10B and 10C and Yellow-Orange Groups 14D, 15D, 16D and 18A).

*Flesh color* (*RHS*2001).—Generally considered bright yellow (Yellow Groups 10A, 10B, 11A, 13B and 13C, Yellow-Orange Groups 14C, 14D, 15C, 15D, 16B, 16C, 16D and 17D) and becoming medium-dark pink near the stone cavity (see 'Stone Cavity Color' for color references). Anthocyanin intensity in the flesh is generally medium next to the skin and weak to medium centrally and next to the stone.

*Flesh fibers*.—Present throughout the flesh.

*Stone cavity color* (*RHS*2001).—Generally considered medium-dark pink. Red Groups 46A and 53A, Red-Purple Groups 58A, 59C, 60A and 60B and Greyed-Purple Group 187C.

*Flesh texture*.—Generally, the flesh is considered firm and fine at commercial maturity.

*Ripening*.—Generally the fruit of the present variety ripens evenly.

*Flavor*.—Considered very sweet (average Brix 13.9) with a rich subacid flavor.

Stone:

*Attachment*.—Semi-freestone at commercial maturity.

*Stone size*.—Generally considered medium relative to the ratio of stone to fruit size. Length — Approximately 28 to 31 mm. Width — Approximately 20 to 22 mm. Thickness — Approximately 16 to 17 mm.

*Fibers*.—Generally, very few fibers are attached sporadically over the surface of the stone.

*Stone form*.—Generally the stone is considered elliptical to ovate.

*Stone base*.—The stone is medium to wide.

*Base angle*.—The base angle of the stone is variable, but most frequently is considered slightly oblique to the stone axis.

*Hilum*.—The hilum is approximately 6 to 7 mm long and less than 1 mm wide.

*Stone apex angle*.—The stone apex is considered medium.

*Stone shape*.—Considered variable. The stone normally ovoid to elongated.

*Stone surface*.—Surface Texture — Consists of single pits, rosettes of pits and chains of pits. Ridges — Numerous fine ridges are present basally and converge towards the base of the stone.

*Ventral edge*.—Considered variable from small to medium.

*Dorsal edge*.—Shape — Grooved and having moderately rough edges.

*Stone color* (*RHS*2001).—The color of the fresh stone is medium to dark brown with medium-dark pink (Greyed-Orange Group 165A, Brown Group 200D, Greyed-Purple Groups 185B, 187C, 187D and Red-Purple Groups 59C, 60A, 60B and 61B. The color of the dry stone is medium brown with dark pink (59A, 59B, 59C, 60A, 60B, 61A and 64A of the Red-Purple Group, 165C and N167D of the Greyed-Orange Group and 187C, 187D of the Greyed-Purple Group). The color of the inside surface of the endocarp is primarily Greyed-Orange Groups 164B and 165B and Greyed-Brown Group N199D.

*Tendency to split*.—Splitting was not observed.

*Kernel*.—The kernel fills the endocarp at harvest and measures approximately 6 mm in thickness, 10 mm in width, and 14-16 mm in length. When dried the shriveled kernels measure approximately 4 mm in thickness, 9-10 mm in width, and 14-15 mm in length. The colors (RHS2001) of the fresh kernels are considered a light to medium brown, Yellow-Orange Group 22A and Greyed-Orange Groups 164B and 165B.

*Use*.—The subject variety, 'TRH3C111', is considered to be a peach tree of early mid-season maturity, which produces firm, yellow-fleshed, subacid fruit which are firm, with 70-90% dark orange red blush over an orange-yellow ground color and which are useful for the fresh fruit market.

*Keeping quality*.—Retains firmness and flavor after 14 days of refrigeration at 3-5° C.

*Resistance to insects and disease*.—No atypical resistances/susceptibilities were noted under normal cultural practices to date.

*Shipping quality*.—Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH3C111', as illustrated and described herein.

* * * * *